United States Patent [19]

Sugiura et al.

[11] 4,003,794
[45] Jan. 18, 1977

[54] PROCESS FOR PRODUCING CHOLESTEROL OXIDASE

[75] Inventors: Mamoru Sugiura, Konan; Hiroshi Shimizu, Nagaokakyo; Masayasu Sugiyama, Kyoto; Takeo Kuratsu, Osaka; Fumio Hirata, Suita, all of Japan

[73] Assignee: Ono Pharmaceutical Co., Ltd., Osaka, Japan

[22] Filed: Dec. 29, 1975

[21] Appl. No.: 645,048

[30] Foreign Application Priority Data

Dec. 27, 1974 Japan .............................. 50-1603

[52] U.S. Cl. .............................. 195/66 R; 195/65
[51] Int. Cl.² ........................................ C12D 13/10
[58] Field of Search ............................ 195/66 R, 65

[56] References Cited

UNITED STATES PATENTS 3,907,642  9/1975  Richmond .......................... 195/62

*Primary Examiner*—Lionel M. Shapiro
*Attorney, Agent, or Firm*—Sughrue, Rothwell, Mion, Zinn & Macpeak

[57] ABSTRACT

A process for producing a cholesterol oxidase comprising cultivating Schizophyllum commune (IFO 4928) in a culture medium and extracting the cholesterol oxidase from the culture filtrate.

2 Claims, No Drawings

PROCESS FOR PRODUCING CHOLESTEROL OXIDASE

BACKGROUND OF THE INVENTION

1. FIELD OF THE INVENTION

The present invention relates to a process for producing a cholesterol oxidase, more particularly, it relates to a process for producing a cholesterol oxidase by cultivating Schizophyllum commune IFO 4928 (deposited at the Fermentation Research Institute Foundation of 54, Jusan-Nishinomachi 4-chome, Higashiyodogawa-ku, Oska City, Japan) and extracting the desired cholesterol oxidase from the culture filtrate.

2. DESCRIPTION OF THE PRIOR ART

It is known that cholesterol oxidases can be produced from some kinds of bacteria, for example, Mycobacterium and Brevibacterium, or from Actinomyces. However, these cholesterol oxidases are unsatisfactory because they have too broad a substrate specificity. More particularly, in obtaining an enzyme that is active only on the hydroxyl group at the 3β-position of cholesterols to oxidize the 3β-hydroxyl group to a ketone group from conventional microorganisms by cultivation, extraction and purification, there are various technical problems which must be solved to put such processes to commercial use.

For instance, the enzymes obtained from Brevibacterium sterolicum are active not only on the 3β-position but also on the 17β-position of cholesterol, and their substrate specificity extends over a very wide range including cholesterol, cholestanol, dihydroergosterol, stigmasterol, testosterone, 5α-androstane-3α,17β-diol and others. Their substrate spectra can be narrowed to a specific one only through several purification stages.

For practical use in evaluating or determining cholesterol with vital material such as tissue and serum, such a wide substrate specificity is not desirable. Therefore, various investigations have been made with a view to finding a cholesterol oxidase which has specificity only on the 3β-position of cholesterol, and it has now been found, as a result of screening various bacteria, such as Eumycetes and Basidiomycetes, that a cholesterol oxidase having a highly distinctive substrate specificity can be obtained from a strain of Schizophyllum commune that has not hitherto been known.

SUMMARY OF THE INVENTION

The present invention provides a process for producing a cholesterol oxidase by cultivating Schizophyllum commune IFO 4928 in a culture medium and extracting the cholesterol oxidase from the culture filtrate.

DETAILED DESCRIPTION OF THE INVENTION

The Schizophyllum commune IFO 4928 used for producing cholesterol oxidase according to the present invention inherently has the ability to produce the cholesterol oxidase in a medium which contains or which is free of cholesterols (the addition of cholesterols to the medium does not affect the yield of cholesterol oxidase).

The medium useful for the cultivation of the microorganism of the present invention comprises, for example, glucose, molasses, waste molasses or a variety of starches, e.g., corn starch, potato starch, as a carbon source, and urea, yeast extract, maltose extract, casein, peptone, corn steep liquor (CSL), soybean powder, or defatted soybean as a nitrogen source. Whether a medium is useful or not can easily be determined by cultivating the Schizophyllum commune IFO 4928 in various mediums comprising cholesterol and detecting the decrease in cholesterol and the increase in 4-cholesten-3-on in the mediums using thin layer chromatography. Any medium which passes the above screening test can be employed as a medium for cultivating the microorganisms of the present invention. Inorganic nitrogen sources do not produce the enzyme of the present invention. A medium preferred for obtaining the desired cholesterol oxidase efficiently and, on an industrial scale economically, consists of soybean powder and CSL, but the present invention is not limited thereto.

Generally used proportions of carbon sources and nitrogen sources (C/N) are from 3/1 to 5/1 in terms of glucose (=C) and polypeptone (=N) where a glucose-polypeptone-yeast extract medium is used, from 4/1 to 4/2 in terms of soybean powder (=C) and CSL (=N) where a soybean powder-CSL medium is used, and 1/3 in terms of soybean oil (=C) and defatted soybean (=N) where a soybean oil-defatted soybean medium is used. Similar proportions are used for other mediums.

The cholesterol oxidase producing microorganisms of the present invention can be cultivated using, e.g., a shake culture, a jar culture and the like. In the case of a shake culture, the cultivation can generally be performed at about 25 to 30° C under atmospheric pressure with shaking at 120 r.p.m. for 6 to 7 days. When a jar culture is used, generally employed conditions are at about 25° to 30° C under a pressure 0.5 kg/cm² higher than atmospheric with shaking at 0 – 200 r.p.m. and aeration at a rate of 1 VVM (volume of air/volume of medium/ minute) for 3 to 5 days.

The cholesterol oxidase produced from the microorganism according to the present invention is present in the culture solution, which, after isolation, is subjected to a conventional treatment such as an ammonium sulfate precipitation, isoelectric point precipitation, solvent precipitation or ion exchange to concentrate and purify it. Generally, ammonium sulfate precipitation can be attained at a concentration of 55% saturation (i.e., 351 g ammonium sulfate/l enzyme solution at 5° C). The usually employed pH range for isoelectric point precipitation is pH 4.4 to 4.5. Examples of solvents employed in solvent precipitation include ethanol, isopropanol, acetone and the like. For example, with 50% (V/V) acetone, complete precipitation of the desired enzyme occurs. Generally employed ion exchange resins include anion exchange resins such as Dowex 1-X1 based (preferred example is Doulite A-101D), which is strongly basic, for absorbing pigments and DEAE-cellulose, which is weakly basic, for absorbing and eluting the enzyme.

There is thus obtained in a high yield the desired enzymatic preparation which has specificity only at the 3β-position of cholesterol and good pH and heat stability.

Studies of the enzymatic-chemical properties of the cholesterol oxidase obtained according to the present invention have revealed that the cholesterol oxidase obtained by ammonium sulfate precipitation, isoelectric point precipitation or ion exchange treatment using Dowex 1-X1 exhibit excellent properties.

The following are the properties of the cholesterol oxidase obtained by the present invention.

1. Actions and substrate specificity

Differing from the conventional cholesterol oxidases obtained from bacteria, e.g., Actinomyces, the cholesterol oxidase of this invention acts only on the hydroxyl group at the 3β-position of cholesterols. A test made, e.g., o-dianisidine, to oxidize it and thus yield color as shown below.

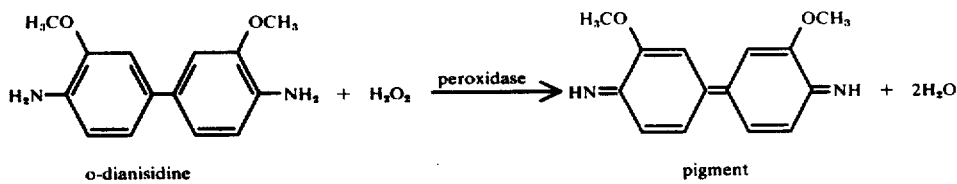

o-dianisidine            pigment for example, by decomposing the hydrogen peroxide liberated from the dehydrogenation of the 3β-position with a peroxidase, bringing the thus generated oxygen into contact with a chromogen such as o-tolidine to form a color, and measuring the absorption spectra thereof in the visible light portion of the spectrum, showed that the present cholesterol oxidase will act on, in addition to cholesterols among the various steroids, sterols having a hydroxyl group at the 3β-position, for example, β-cytosterol, 5-pregnene-3β-ol-20-on, dehydroepiandrostene, 5α-cholestane3β-ol, ergosterol, 7-dehydrocholesterol, 16-dehydropregnelone, 5α-pregnane-3β,20β-diol, 5 -androstane-3β,17β-diol and 5-androstene-3β,17β-diol. The cholesterol oxidase of the present invention does not react on sterols having a hydroxyl group in other positions, i.e., it specifically acts only on the OH in the 3β-position. This property is advantageous in a cholesterol test, as the vital specimen used for this test does not substantially contain any substances other than cholesterol in an appreciable amount.

The enzyme of the present invention reacts directly with cholesterol without relying and NAD (nicotinamide adenine dinucleotide) to produce 4-cholesten-3-one, as confirmed by comparison with the chemically synthesized material through elemental analysis, IR, UV, NMR, mass spectrometry and thin layer chromatography. The pH range of cholesterol activity is at a range more acidic than that of conventional cholesterol oxidases.

2. Optimum pH for cholesterol oxidase activity: pH 4 to 7;

3. pH stability for cholesterol oxidase activity: pH 4 to 9;

4. Heat stability: stable up to 50° C; rapidly losing activity at 60° C and above;

5. Determination of enzymatic activity

The enzymatic activity was determined by measurement of the specific absorption at 245 nm of the 4-cholesten-3-on produced by the reaction of the enzyme solution on the substrate cholesterol.

6. Quantitative determination of serum cholesterol

A sample serum was pretreated by subjecting it to the action of a cholesterol ester decomposing enzyme (e.g., lipoprotein lipase produced from Pseudomonas) to convert ester type cholesterol contained therein to free type cholesterol and then subjected to the action of the cholesterol oxidase of the present invention using a 0.4M phosphate buffer (pH 5.2) at 37° C (the above conversion or pretreatment is necessary since, generally, in a serum there are two forms of cholesterol, i.e., esterified and free cholesterols and cholesterol oxidase can act only on free cholesterols). The hydrogen peroxide produced was decomposed with a peroxidase and the oxygen generated was accepted by a chromogen, A good correlation was observed between the results with respect to quantitative determination of serum cholesterol obtained by the above method and those obtained by the conventional Zak-Henly modified method.

The following Examples are given to illustrate the present invention without limiting its scope. Unless otherwise indicated, all parts, percents, ratios and the like are by weight, the pressure employed is atmospheric pressure and all systems are aqueous.

EXAMPLE 1

50 aliquots each containing 100 ml of a shake culture of Schizophyllum commune IFO 4928 was inoculated in a 100 l culture solution (pH 5 – 6) containing 1% polypeptone, 0.1% yeast extract and 4% glucose (therefore the proportion of inoculant is 5% on a v/v basis), and cultivation was performed at 29° C for 4 days with shaking using a shaking apparatus at a rate of 120 r.p.m. or stirring with air bubbles supplied at a rate of 1 VVM. Solid substances were then separated from the fermented liquid by filtration using a filter press and centrifugal precipitation. To the supernate of the filtrate, ammonium sulfate was added at about 5° C until 55% saturation was obtained. The ammonium sulfate precipitate formed was subjected to dialysis with a mixture of 1/100 M phosphoric acid buffer solution (pH 7.0) and 0.1 mM of EDTA. The resultant product was frozen in a freezer at about −20° C and thawed by immersion in water at about 15° C for 2 to 3 hours to remove the precipitate formed. Ammonium sulfate was added at about 5° C to 60% saturation and the precipitate formed was subjected to dialysis with the above buffer solution. After freeze-drying there was obtained faintly brownish enzyme in the form of a powder at a yield of 3,000 to 5,000 units from 100 liters of the fermented aqueous solution.

EXAMPLE 2

Following the essential procedure of Example 1 unless otherwise indicated, Schizophyllum commune IFO 4928 was inoculated in a culture solution (pH 4 – 5) comprising 3% soybean and 1% corn steep liquor and cultivation was conducted at 29° C for 4 days with shaking or stirring with air. The fermented liquid was then filtered and then processed as in Example 1 to obtain the enzyme at a yield of 4,000 to 8,000 units from 100 liters of the fermented liquid.

EXAMPLE 3

Following the essential procedure of Example 1 unless otherwise indicated, Schizophyllum commune IFO 4928 was inoculated in the same proportion as in Example 1 in a culture solution (pH 4.5) comprising 3% defatted soybean, 1% soybean oil and 0.25% 8N NaOH. Cultivation was performed at 26° C for 4 to 5 days with shaking or stirring with air. Solid substances were removed from the fermented liquid by filtration or centrifugal separation. The pH of the supernate of the filtrate was adjusted to 4.4 to 4.5 with acetic acid. The precipitate formed was suspended in water and the pH of the suspension was adjusted to 6 to 7 with NaOH. The suspension was then freezethawed and the precipitate which formed removed. The supernate was passed through Dowex 1-X1 (Cl type) and ammonium sulfate was added at about 5° C to 60% saturation. In more detail, Dowex 1-X1 is the tradename for a strongly basic anion exchange resin, produced by Dow Chemical Co., comprising styrene and divinylbenzene groups as major recurring units and having quaternary ammonium groups as the ion-exchanging group. The Dowex 1-X1 in a columm was converted to the Cl-type and then washed with 1/50 M phosphoric acid. To the resulting ionexchange resin the enzyme preparation was charged to adsorb proteins other than the cholesterol oxidase of this invention. The precipitate produced was then subjected to dialysis with a 1/100 M phosphoric acid buffer solution (pH 7.0), followed by freeze-drying. The yield was 4,000 to 8,000 units from 100 liters of the fermented liquid, as in Example 2.

While the invention has been described in detail and with reference to specific embodiments thereof, it will be apparent to one skilled in the art that various changes and modifications can be made therein without departing from the spirit and scope thereof.

What is claimed is:

1. A process for producing a cholesterol oxidase, which comprises cultivating Schizophyllum commune (IFO 4928) in a culture medium and extracting the cholesterol oxidase from the culture filtrate.

2. The process of claim 1, wherein cultivating is at a pH of 4 to 7.

* * * * *